US007445800B2

(12) United States Patent
Morris et al.

(10) Patent No.: US 7,445,800 B2
(45) Date of Patent: Nov. 4, 2008

(54) METHOD FOR REMEDIATING MOLD AND MILDEW USING ACIDIC ELECTROLYZED WATER

(75) Inventors: Chad D. Morris, American Fork, UT (US); James K. Stone, Lindon, UT (US)

(73) Assignee: EAU Technologies, Inc., Kennesaw, GA (US)

( * ) Notice: Subject to any disclaimer, the term of this patent is extended or adjusted under 35 U.S.C. 154(b) by 613 days.

(21) Appl. No.: 10/877,322

(22) Filed: Jun. 25, 2004

(65) Prior Publication Data

US 2004/0265394 A1 Dec. 30, 2004

Related U.S. Application Data

(60) Provisional application No. 60/482,368, filed on Jun. 25, 2003.

(51) Int. Cl.

| | |
|---|---|
| ***A01N 59/00*** | (2006.01) |
| ***A01N 61/00*** | (2006.01) |
| ***A61L 2/03*** | (2006.01) |
| ***A61L 2/18*** | (2006.01) |
| ***C02F 1/461*** | (2006.01) |
| ***C25B 1/26*** | (2006.01) |

(52) U.S. Cl. .......................... 424/661; 422/29; 422/37; 205/556; 205/742

(58) Field of Classification Search .................. 424/661
See application file for complete search history.

(56) References Cited

U.S. PATENT DOCUMENTS

| | | | | |
|---|---|---|---|---|
| 6,610,249 | B1 | 8/2003 | Hinze | |
| 7,001,493 | B1 * | 2/2006 | Kim | 204/252 |
| 2003/0200998 | A1 * | 10/2003 | Hoenisch et al. | 134/22.12 |
| 2005/0211643 | A1 * | 9/2005 | Phillips et al. | 210/753 |

OTHER PUBLICATIONS

Sutin, K., "Big Job Needs a Power Wash," St. Louis Post-Dispatch, Apr. 13, 2002, p. L8 [obtained online from ProQuest on Oct. 5, 2007].*

Sell, S., "Awash in New-Found Power," USA Today, Apr. 30, 1999, p. 8D [obtained online from ProQuest on Oct. 5, 2007].*

Kiura, H. et al., "Bactericidal activity of electrolyzed acid water from solution containing sodium chloride at low concentration, in comparison with that at high concentration," Journal of Microbiological Methods, vol. 49, pp. 285-293 (2002).*

HCAPLUS abstract, accession No. 2000:536737 (2000).*

Nagamatsu, Y. et al., "Durability of bactericidal activity in electrolyzed neutral water by storage," Dental Materials Journal, vol. 21(2), pp. 93-104 (2002).*

* cited by examiner

*Primary Examiner*—John Pak
(74) *Attorney, Agent, or Firm*—Bracewell & Giuliani LLP

(57) ABSTRACT

Methods for remediating mold and mildew are provided using acidic electrolyzed water. Acidic electrolyzed A water, electrolyzed C water or combination of electrolyzed A and C water is released into an infected area through a high pressure sprayer, a mister or an electrostatic sprayer. Upon contacting the infected area, mold and mildew growing in the infected area is remedied.

6 Claims, No Drawings

METHOD FOR REMEDIATING MOLD AND MILDEW USING ACIDIC ELECTROLYZED WATER

CROSS-REFERENCES TO RELATED APPLICATIONS

This non-provisional patent application claims the benefit of U.S. Provisional Application Ser. No. 60/482,368, filed Jun. 25, 2003.

TECHNICAL FIELD OF THE INVENTION

This invention relates in general to cleaning and disinfecting. More particularly, this invention relates to a method of mold and mildew remediation using acidic electrolyzed oxidizing water.

SUMMARY OF THE INVENTION

The present invention is directed to a method for remediating mold and mildew in an infected area using high pressure washing. This method advantageously includes spraying acidic electrolyzed water onto the surface of the infected area using a high pressure sprayer to wash the infected area. This method can further advantageously include a step of scrubbing the infected area.

The present invention is also directed to a method for remediating mold and mildew in an infected area using an acidic electrolyzed water mist. This method advantageously includes releasing acidic electrolyzed water into the air in the infected area using a mister to form acidic electrolyzed water mist. Upon contacting the infected area, the acidic electrolyzed water mist remedies mold and mildew in the infected area.

This method can be used to clean infected air ducts by brushing the ducts with a brush while the acidic electrolyzed water mist is being released from a mister into the ducts. The acidic electrolyzed water mist mixes with the brush, thereby remedies mold and mildew along the brush path in the infected air ducts.

The present invention is further directed to a method for remediating mold and mildew in an infected area using electrostatic spraying. This method advantageously includes releasing acidic electrolyzed water into the air in the infected area using an electrostatic sprayer to form micro droplets of acidic electrolyzed water. The micro droplets of acidic electrolyzed water reacts with mold and mildew in the infected area, thereby cleans the area.

DETAILED DESCRIPTION OF THE INVENTION

The present invention uses acidic electrolyzed water, referred to herein as A and C types, to clean mold and mildew. Electrolyzed A water has an oxidative/reduction potential (ORP) of 1,160-1,170$^+$ mV and a pH of 1.8-2.4. It contains 10-150 or up to 200 ppm hypochlorous acid (HOCl), which is a powerful oxidizing agent. Such high level of HOCl provides premium condition for killing mold, yet is still non-toxic to humans. Electrolyzed C water has ORP of 850 mV and a pH of up to 5. Type C water also contains HOCl at a level in the range mentioned above. Type C water is stabilized A water with a longer shelf life.

Electrolyzed water ("EO water") is produced by an electrolysis generator that produces some chlorine gas. Some of the chlorine gas reacts to form the HOCl. The electrolysis generator also simultaneously produces an alkaline water stream, referred to herein as type B. The pH of the EO water may be controlled by blending some of the type B water back into the water entering the electrolysis cells. This raises the pH of the water entering the cells. Sufficient alkaline water is recirculated and mixed with the water entering the electrolysis cells to produce type C EO water with a pH of approximately 5.

To determine the safeness for use, type A water with a HOCl concentration of 70 ppm was evaluated for primary skin irritation in accordance with the guidelines of the International Organization for Standardization 10993: Biological Evaluation of Medical Devices, Part 10: Test for Irritation and Sensitization. Portions of the test article and control article were topically applied to the skin of rabbits and left in place for 24 hours. The sites were graded for erythema and edema at 1, 24, 48 and 72 hours after removal of the single sample application.

Under the above testing conditions, no erythema and edema were observed on the skin of the rabbits. The Primary Irritation Index for the test article was calculated to be 0.0. The response of the test article was categorized as negligible.

Type A water was also evaluated for the potential to cause vaginal mucosal irritation. This study was conducted in accordance with the requirements of the International Organization for Standardization 10993: Biological Evaluation of Medical Devices, Part 10: Test for Irritation and Sensitization. Testing Rabbits received a daily 2 ml intravaginal treatment of the test article for 5 consecutive days. Control rabbits were similarly treated with 0.9% sodium chloride USP solution. The animals were euthanized the day following the last treatment. Each vagina was removed and evaluated macroscopically and microscopically. Under the above testing conditions, the test articles were considered a nonirritant to the vaginal mucosal tissue of the rabbits.

With the skin irritation and vaginal mucosal irritation test results being safe, electrolyzed A water or C water is used to treat mold and mildew. One method is to use high pressure washing. Full strength electrolyzed A water or C water is sprayed under the room temperature with a conventional high pressure sprayer directly unto the visibly infected areas or areas where mold or mildew is suspected to have grown. The high pressure spray is directly typically onto areas that would not be damaged by being wetted with the spray, such as floors, cabinets and certain appliances. Mold and mildew is killed immediately upon contacting the acidic EO water spray. Usually no scrubbing is needed unless the mold is densely accumulated with high visibility and growing off a wall.

Another method of treating mold and mildew is to use a cold mister or fogger to release electrolyzed A water or C water into the air. The entire room is misted with a conventional mister or fogger. The mist will come into contact with the floor, walls, ceiling, cabinets, and furniture. The mist will also come into contact with fabrics in the room, such as drapes, carpet and upholstered furniture. However, the duration of the misting is not long, typically only a few minutes, thus no damage occurs to the fabric. Air borne mold is instantly killed by the mist as well as mold on the floor, walls, ceiling, cabinets, and furniture.

The fogging method can be used for cleaning air ducts where mold and mildew is suspected to have grown. A brush can be used to run down the duct while a mister or fogger releases electrolyzed A water or C water into the duct. The opposite end of the duct from the mister is typically sealed. As the brush runs down the duct, acidic EO water mist will mix with the brush and kill mold and mildew growing in the duct along the brush path, thereby cleaning the air duct. The fogger could also be incorporated with the brush so that it moves along the duct with the brush.

Also, a conventional electrostatic sprayer can be used to spray electrolyzed A water or C water unto the infected areas. Acidic EO water is first added to the sprayer. Once the sprayer is triggered, the acidic EO water exits the sprayer. Micro droplets of water are formed upon the release of electrolyzed A water. Such droplets have negative charges and will react with positively charged particles growing in the air including mold and mildew. Electrostatic spraying is a magnetic process commonly used in car painting and carpet dying.

Some mold infected buildings may require pressure washing, fogging and electrostatic spraying as well as air duct cleaning. An air test is performed before and after the treatment to ensure that the mold and mildew has been removed from the air after the treatment, thus is clean and safe for living.

Although only electrolyzed A water has been tested so far with positive results, C water is anticipated to perform the same tasks with the same positive effect.

The present invention is directed to a method for remediating mold and mildew in an infected area using high pressure washing. This method advantageously includes spraying acidic electrolyzed water onto the surface of the infected area using a high pressure sprayer to wash the infected area. This method can further advantageously include a step of scrubbing the infected area.

In this method, acidic electrolyzed water used can be electrolyzed A water, electrolyzed C water, or combination of electrolyzed A and C water. The electrolyzed A water preferably has an oxidative/reduction potential of about $1,160^{+}$-1, $170^{+}$ mV and a pH of about 1.8-2.4. Such electrolyzed A water preferably contains about 10-200 ppm of hypochlorous acid. The electrolyzed C water preferably has an oxidative/reduction potential of about $850^{+}$ mV and a pH of up to about 5. Such electrolyzed C water preferably contains about 10-200 ppm of hypochlorous acid.

The present invention is also directed to a method for remediating mold and mildew in an infected area using an acidic electrolyzed water mist. This method advantageously includes releasing acidic electrolyzed water into the air in the infected area using a mister to form acidic electrolyzed water mist. Upon contacting the infected area, the acidic electrolyzed water mist remedies mold and mildew in the infected area.

This method can be used to clean infected air ducts by brushing the ducts with a brush while the acidic electrolyzed water mist is being released from a mister into the ducts. The acidic electrolyzed water mist mixes with the brush, thereby remedies mold and mildew along the brush path in the infected air ducts.

In this method, acidic electrolyzed water used can be electrolyzed A water, electrolyzed C water, or combination of electrolyzed A and C water. The electrolyzed A water preferably has an oxidative/reduction potential of about $1,160^{+}$-1, $170^{+}$ mV and a pH of about 1.8-2.4. Such electrolyzed A water preferably contains about 10-200 ppm of hypochlorous acid. The electrolyzed C water preferably has an oxidative/reduction potential of about $850^{+}$ mV and a pH of up to about 5. Such electrolyzed C water preferably contains about 10-200 ppm of hypochlorous acid.

The present invention is further directed to a method for remediating mold and mildew in an infected area using electrostatic spraying. This method advantageously includes releasing acidic electrolyzed water into the air in the infected area using an electrostatic sprayer to form micro droplets of acidic electrolyzed water. The micro droplets of acidic electrolyzed water reacts with mold and mildew in the infected area, thereby cleans the area.

In this method, acidic electrolyzed water used can be electrolyzed A water, electrolyzed C water, or combination of electrolyzed A and C water. The electrolyzed A water preferably has an oxidative/reduction potential of about $1,160^{+}$-1, $170^{+}$ mV and a pH of about 1.8-2.4. Such electrolyzed A water preferably contains about 10-200 ppm of hypochlorous acid. The electrolyzed C water preferably has an oxidative/reduction potential of about $850^{+}$ mV and a pH of up to about 5. Such electrolyzed C water preferably contains about 10-200 ppm of hypochlorous acid.

While the invention has been shown or described in only some of its forms, it should be apparent to those skilled in the art that it is not so limited, but is susceptible to various changes without departing from the scope of the invention.

What is claimed is:

1. A method for remediating mold and mildew in an infected area, comprising the step of:

spraying acidic electrolyzed water onto the surface of the infected area using a high pressure sprayer to wash the infected area, thereby remediating mold and mildew in the infected area;

wherein the acidic electrolyzed water has an oxidative/reduction potential of about $1,160^{+}$-$1,170^{+}$ mV and a pH of about 1.8-2.4, and contains about 10-200 ppm of hypochlorous acid.

2. The method of claim 1, the method further comprising the step of:

scrubbing the infected area.

3. A method for remediating mold and mildew in an infected area, comprising the step of:

spraying acidic electrolyzed water onto the surface of the infected area using a high pressure sprayer to wash the infected area, thereby remediating mold and mildew in the infected area;

wherein the acidic electrolyzed water has a stabilized oxidative/reduction potential of about $850^{+}$ mV and a pH of up to about 5, and contains about 10-200 ppm of hypochlorous acid.

4. The method of claim 3, the method further comprising the step of:

scrubbing the infected area.

5. A method for remediating mold and mildew in an infected area, comprising the step of:

spraying acidic electrolyzed water onto the surface of the infected area using a high pressure sprayer to wash the infected area, thereby remediating mold and mildew in the infected area, wherein the acidic electrolyzed water comprises:

water having an oxidative/reduction potential of about $1,160^{+}$-$1,170^{+}$ mV and a pH of about 1.8-2.4, and contains about 10-200 ppm of hypochlorous acid; and water having a stabilized oxidative/reduction potential of about $850^{+}$ mV and a pH of up to about 5, and contains about 10-200 ppm of hypochlorous acid.

6. The method of claim 5, the method further comprising the step of:

scrubbing the infected area.

* * * * *